(12) United States Patent
Zhang et al.

(10) Patent No.: US 10,390,749 B2
(45) Date of Patent: Aug. 27, 2019

(54) METHOD AND DEVICE FOR MONITORING FATIGUED DRIVING

(71) Applicant: BOE TECHNOLOGY GROUP CO., LTD., Beijing (CN)

(72) Inventors: Jingyu Zhang, Beijing (CN); Wei Sun, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 23 days.

(21) Appl. No.: 15/510,854

(22) PCT Filed: Feb. 23, 2016

(86) PCT No.: PCT/CN2016/074316
§ 371 (c)(1),
(2) Date: Mar. 13, 2017

(87) PCT Pub. No.: WO2016/161850
PCT Pub. Date: Oct. 13, 2016

(65) Prior Publication Data
US 2017/0281068 A1 Oct. 5, 2017

(30) Foreign Application Priority Data
Apr. 10, 2015 (CN) .......................... 2015 1 0170673

(51) Int. Cl.
*A61B 5/18* (2006.01)
*G08B 21/06* (2006.01)
(Continued)

(52) U.S. Cl.
CPC .................. *A61B 5/18* (2013.01); *A61B 3/10* (2013.01); *A61B 5/0077* (2013.01); *A61B 5/022* (2013.01);
(Continued)

(58) Field of Classification Search
CPC ............................................ B60W 2040/0827
See application file for complete search history.

(56) References Cited

U.S. PATENT DOCUMENTS

| | | | |
|---|---|---|---|
| 6,575,902 B1* | 6/2003 | Burton | A61B 5/18 340/575 |
| 2007/0100666 A1* | 5/2007 | Stivoric | F24F 11/30 705/3 |

(Continued)

FOREIGN PATENT DOCUMENTS

| | | |
|---|---|---|
| CN | 2693220 Y | 4/2005 |
| CN | 2822608 Y | 10/2006 |

(Continued)

OTHER PUBLICATIONS

Search Report and Written Opinion dated May 27, 2016 from State Intellectual Property Office of the P.R. China.

(Continued)

*Primary Examiner* — Scott Luan
(74) *Attorney, Agent, or Firm* — Dilworth & Barrese, LLP.; Michael J. Musella, Esq.

(57) ABSTRACT

A method and device for monitoring fatigued driving. The device comprises a processor, a monitoring unit an alarm unit and an inflating unit connected to the processor. The processor is used to obtain a monitor result, transmit, according to the monitor result, an alarm instruction to the alarm unit, and transmit an air inflation instruction to inflating unit upon obtaining the monitor result again after transmitting the alarm instruction. The monitor unit is used to monitor, in real time, a driving state of the driver, and transmit data indicating the driving state of the driver; the alarm unit (12) is used to receive the alarm instruction, and provide the alarm according to the alarm instruction; and the (Continued)

inflating unit is used to receive the air inflation instruction, and fill air according to the air inflation instruction.

17 Claims, 6 Drawing Sheets

(51) Int. Cl.
    *A61B 3/10*       (2006.01)
    *A61B 5/022*     (2006.01)
    *A61B 5/0476*   (2006.01)
    *A61M 21/00*    (2006.01)
    *A61B 5/00*       (2006.01)
    *A61B 5/11*       (2006.01)
    *A61B 5/01*       (2006.01)
    *A61B 5/048*     (2006.01)
    *B60K 28/06*     (2006.01)
    *B60W 40/08*    (2012.01)

(52) U.S. Cl.
    CPC .......... *A61B 5/0476* (2013.01); *A61B 5/1103* (2013.01); *A61M 21/00* (2013.01); *G08B 21/06* (2013.01); *A61B 5/01* (2013.01); *A61B 5/048* (2013.01); *A61B 5/7282* (2013.01); *A61B 2560/029* (2013.01); *A61B 2562/0219* (2013.01); *B60K 28/066* (2013.01); *B60W 2040/0827* (2013.01)

(56) References Cited

U.S. PATENT DOCUMENTS

2010/0134302 A1    6/2010    Ahn et al.
2015/0008710 A1*  1/2015    Young .................... B60N 2/914
                                                297/217.3

FOREIGN PATENT DOCUMENTS

| | | |
|---|---|---|
| CN | 103111020 A | 5/2013 |
| CN | 103318023 A | 9/2013 |
| CN | 203318275 U | 12/2013 |
| CN | 203338530 U | 12/2013 |
| CN | 103680065 A | 3/2014 |
| CN | 103818256 A | 5/2014 |
| CN | 102274032 A | 12/2014 |
| CN | 104505922 A | 4/2015 |
| CN | 204390429 U | 6/2015 |
| CN | 104840204 A | 8/2015 |
| JP | 201099143 A | 5/2010 |

OTHER PUBLICATIONS

Chinese Office Action dated Dec. 28, 2016.
Second Chinese Office Action dated Jun. 16, 2017.

* cited by examiner

METHOD AND DEVICE FOR MONITORING FATIGUED DRIVING

TECHNICAL FIELD

Embodiments of the present disclosure relate to a method and device for monitoring fatigue driving.

BACKGROUND

It is well-known that fatigue driving is one of the major factors that cause most traffic accidents, and so how to prevent fatigue driving has gradually become a focus of attention.

A fatigue driving warning system in existing technologies can only give out a simple warning to a driver when it detects that the driver is in a fatigue driving state. However, when the driver is in an over-fatigue state, the warning may not be able to effectively help the driver to restore from the fatigue driving state to a clearheaded driving state, such that safety problems that may emerge when the driver is in the fatigue driving state still cannot be effectively avoided.

SUMMARY

Embodiments of the present disclosure provide a method and a device for monitoring fatigue driving, which can increase a probability that the driver restores from a fatigue driving state to a clearheaded driving state, and hence can reduce a probability of occurrence of safety problems when the driver is in the fatigue driving state.

Embodiments of the disclosure provides a device for monitoring fatigue driving, which includes a processor, and a monitoring unit, an alarm unit and an inflating unit which are respectively connected with the processor. For example, the processor is configured to acquire a monitoring result, send an alarm instruction to the alarm unit according to the monitoring result, and send an inflating instruction to the inflating unit when acquiring the monitoring result again after sending the alarm instruction, where the monitoring result is used for indicating whether a driver is in a fatigue driving state, the alarm instruction is used for instructing the alarm unit to give out an alarm, and the inflating instruction is used for instructing the inflating unit to perform an inflation operation; the monitoring unit is configured to monitor the driving state of the driver in real time, and send data indicating the driving state of the driver to the processor; the alarm unit is configured to receive the alarm instruction sent by the processor, and give out the alarm according to the alarm instruction; and the inflating unit is configured to receive the inflating instruction sent by the processor, and perform the inflation operation according to the inflating instruction.

For example, the inflating unit includes a microprocessor connected with the processor, a driving module connected with the microprocessor, and a cuff connected with the driving module. The microprocessor is configured to receive the inflating instruction sent by the processor, and send an inflating signal to the driving module according to the inflating instruction; and the driving module is configured to receive the inflating signal sent by the microprocessor, and inflate the cuff according to the inflating signal.

For example, the inflating unit further includes a pressure sensor connected with both the microprocessor and the cuff. The pressure sensor is configured to detect a value of a pressure intensity of the cuff when the driving module inflates the cuff, and send the value of the pressure intensity to the microprocessor; the microprocessor is also configured to receive the value of the pressure intensity sent by the pressure sensor, and send a deflating signal to the driving module when the value of the pressure intensity is greater than or equal to a default threshold; and the driving module is also configured to receive the deflating signal sent by the microprocessor, and deflate the cuff according to the deflating signal.

For example, the driving module is a miniature inflation motor; or the driving module includes a miniature pressure pump and a miniature exhaust valve.

For example, the monitoring unit includes at least one of a face monitoring module or a brain monitoring module; the face monitoring module is configured to monitor eyes of the driver and send data indicating an eye state of the driver to the processor; and the brain monitoring module is configured to monitor a brain of the driver and send data indicating a brain state of the driver to the processor.

For example, the face monitoring module is a miniature camera; and the brain monitoring module is an electroencephalogram (EEG) sensor.

For example, the device for monitoring fatigue driving further comprises a power supply unit connected with the processor, the monitoring unit, the alarm unit and the inflating unit; and the power supply unit is configured to supply power for the processor, the monitoring unit, the alarm unit and the inflating unit.

For example, the power supply unit is charged by a wireless charging approach.

For example, the device for monitoring fatigue driving further comprises a switching unit connected with the processor; and the switching unit is configured to control the device for monitoring fatigue driving to switch on or off.

For example, the switching unit is a mechanical switch or an acceleration sensor.

For example, the alarm unit includes at least one of a voice alarm module or a vibrating motor alarm module.

Embodiments of the disclosure provide a method for monitoring fatigue driving, applied in a device for monitoring fatigue driving described herein, which includes: monitoring, by the device for monitoring fatigue driving, a driving state of a driver in real time; providing, by the device for monitoring fatigue driving, an alarm if the driving state of the driver is determined to be a fatigue driving state; and performing, by the device for monitoring fatigue driving, an inflation operation if the driving state of the driver is still determined to be the fatigue driving state after providing the alarm.

For example, performing, by the device for monitoring fatigue driving, the inflation operation if the driving state of the driver is still determined to be the fatigue driving state after providing the alarm includes: inflating a cuff of the device for monitoring fatigue driving if the driving state of the driver is still determined to be the fatigue driving state after providing the alarm.

For example, the method further comprises: detecting, by the device for monitoring fatigue driving, a value of a pressure intensity of the cuff when the cuff is inflated; and deflating the cuff if the value of the pressure intensity is greater than or equal to a default threshold.

For example, monitoring, by the device for monitoring fatigue driving, the driving state of a driver in real time includes: monitoring, by the device for monitoring fatigue driving, eyes of the driver and a brain of the driver in real time; and performing, by the device for monitoring fatigue driving, the inflation operation if the driving state of the driver is still determined to be the fatigue driving state after providing the alarm includes: providing, by the device for monitoring fatigue driving, the alarm if both the eyes of the driver and the brain of the driver are determined to be in a fatigue state.

For example, monitoring, by the device for monitoring fatigue driving, the eyes of the driver and the brain of the driver in real time includes: extracting, by the device for monitoring fatigue driving, eye features of the driver in real time, and acquiring an EEG signal of the driver; determining, by the device for monitoring fatigue driving, whether the eyes of the driver are in the fatigue state according to the eye features; and determining, by the device for monitoring fatigue driving, whether the brain of the driver is in the fatigue state according to the EEG signal.

BRIEF DESCRIPTION OF THE DRAWINGS

In order to illustrate the technical solutions in the embodiments of the present disclosure or the existing arts more clearly, the drawings need to be used in the description of the embodiments or the existing arts will be briefly described in the following; it is obvious that the drawings described below are only related to some embodiments of the present disclosure, for one ordinary skilled person in the art, other drawings can be obtained according to these drawings without making other inventive work.

DETAILED DESCRIPTION

Hereafter, the technical solutions of the embodiments of the present disclosure will be described in a clearly and fully understandable way in connection with the drawings related to the embodiments of the disclosure. It is obvious that the described embodiments are just a part but not all of the embodiments of the present disclosure. Based on embodiments of the present disclosure, all other embodiments obtained by those skilled in the art without making other inventive work should be within the scope of the present disclosure.

Detailed description will be given below to a method and a device for monitoring fatigue driving, provided by embodiments of the present disclosure, with reference to the accompanying drawings.

In some technical solutions, a device for monitoring fatigue driving (or a warning system for fatigue driving) comprises a central processing unit (CPU), a fatigue driving warning light, a voice reminder, a hand blood pressure sensor, a foot blood pressure sensor and a body temperature sensor which are electrically connected with the CPU respectively, and a power source for supplying power to the various power consumption components described above. The device (or the system) may monitor life parameters, including a time duration when a driver sits on a driver seat, a body temperature of the driver, a hand blood pressure and a foot blood pressure, etc., in real time. The life parameters may reflect a current physical status of the driver in real time. For instance, the hand blood pressure and the foot blood pressure may indicate whether the driver has insufficient blood pressure and whether hand and/or foot paralysis occurs. After the CPU collects and analyzes the life parameters, the fatigue driving warning light and the voice reminder may provide a warning message to the driver so that a warning indicating whether the driver has been in the fatigue driving state may be provided in time to the driver, and another warning indicating possible occurrence of paroxysmal diseases may also be provided to the driver.

Figure 1:
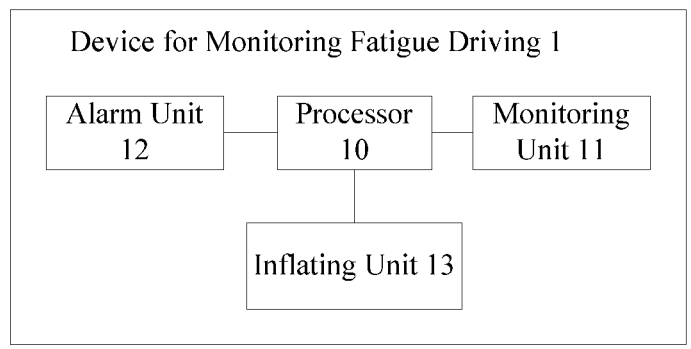
FIG. 1 is a first schematic structural view of a device for monitoring fatigue driving provided by an embodiment of the present disclosure.

As illustrated in FIG. 1, an embodiment of the present disclosure provides a device 1 for monitoring fatigue driving. The device 1 for monitoring fatigue driving may comprise a processor 10, a monitoring unit 11, an alarm unit 12 and an inflating unit 13, where the monitoring unit 11, the alarm unit 12 and the inflating unit 13 are respectively connected to the processor 10.

For instance, the processor 10 is configured to acquire a monitoring result, send an alarm instruction to the alarm unit 12 according to the monitoring result, and send an inflating instruction to the inflating unit 13 when acquiring the monitoring result again after sending the alarm instruction, in which the monitoring result indicates whether the driver is in the fatigue driving state, the alarm instruction is used for instructing the alarm unit 12 to provide an alarm signal; and the inflating instruction is used for instructing the inflating unit 13 to perform an inflating operation.

The monitoring unit 11 is configured to monitor in real time or in near real time a driving state of the driver, and send data indicating the driving state of the driver to the processor 10.

The alarm unit 12 is configured to receive the alarm instruction sent by the processor 10, and provide an alarm signal according to the alarm instruction. For instance, the alarm signal may include a voice prompt, a lighting alert or a vibrating alert.

The inflating unit 13 is configured to receive the inflating instruction sent by the processor 10, and perform an inflating operation according to the inflating instruction.

The device for monitoring fatigue driving provided by embodiments of the present disclosure may monitor the driving state of the driver in real time, may prompt the driver through the alarm signal when the driver is in the fatigue driving state, and may also perform an inflating operation when the driver continues to be in the fatigue driving state. The inflating operation helps the driver to restore from the fatigue driving state to a clearheaded driving state. The device for monitoring fatigue driving provided by embodiments of the present disclosure can increase a probability that the driver restores from the fatigue driving state to the clearheaded driving state, and hence can reduce a probability of occurrence of safety problems when the driver is in the fatigue driving state.

It is noted that the device for monitoring fatigue driving provided by the embodiments of the present disclosure may be worn on the driver's head. When the inflating unit 13 performs an inflating operation, gas introduced by the inflating unit may apply pressure on the driver's head and help to increase the amount of blood supply on the driver's head, which is helpful for the driver to restore from the fatigue driving state to the clearheaded driving state.

For instance, the device for monitoring fatigue driving provided by the embodiments of the present disclosure may be a small-sized monitoring device which can be worn on the driver's head, e.g., a hat, a headphone, a barrette and a hair lace, etc.

For instance, a method of acquiring the monitoring result by the processor 10 in the embodiments of the present disclosure may include any of the following:

(1) The processor 10 receives the monitoring result sent by the monitoring unit 11. For instance, the data indicating the driving state of the driver, sent by the monitoring unit 11 to the processor 10, is the monitoring result. For instance, the processor 10 directly receives the monitoring result sent by the monitoring unit 11. In another instance, the monitoring unit 11 monitors the driving state of the driver in real time and may send the obtained monitoring result to the processor 10 when the driver is in the fatigue driving state, and the processor 10 may provide an alarm instruction according to the monitoring result after acquiring the monitoring result.

(2) After receiving the data indicating the driving state of the driver sent by the monitoring unit 11, the processor 10 analyzes and processes the data and obtains a processing result, and then acquires the monitoring result from the processing result. For instance, the data indicating the driving state of the driver, sent by the monitoring unit 11 to the processor 10, is data relevant to the driver including, e.g., eye features, facial features and/or electroencephalograph (EEG) signals of the driver monitored in real time by the monitoring unit 11. The processing result may include a first monitoring result indicating that the driver is in the fatigue driving state or a second monitoring result indicating that the driver is in the clearheaded driving state (is not in the fatigue driving state). In embodiments of the present disclosure, after the processor 10 obtains the processing result, if the processing result is the second monitoring result, the processor 10 may not take any action; and if the processing result is the first monitoring result, the processor 10 may provide an alarm instruction according to the first monitoring result after acquiring the first monitoring result.

Figure 2:
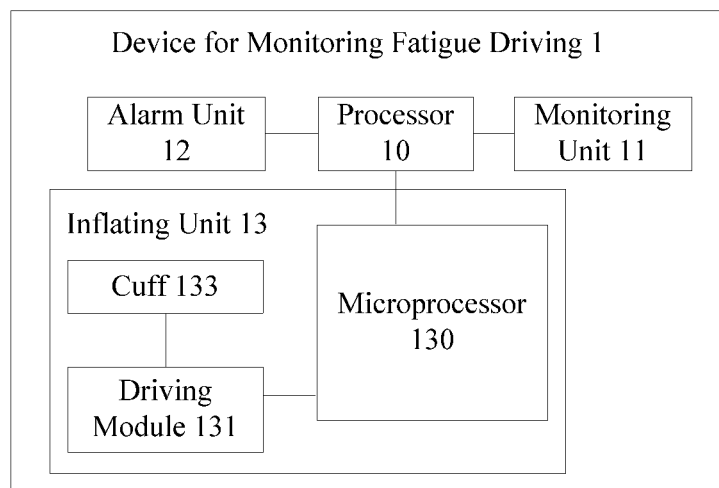
FIG. 2 is a second schematic structural view of a device for monitoring fatigue driving provided by an embodiment of the present disclosure.

For instance, as shown in FIG. 2, the inflating unit 13 may include a microprocessor 130 connected with the processor 10, a driving module 131 connected with the microprocessor 130, and a cuff 133 connected with the driving module 131.

For instance, the microprocessor 130 may be configured to receive the inflating instruction sent by the processor 10, and send an inflating signal to the driving module 131 according to the inflating instruction.

The driving module 131 may be configured to receive the inflating signal sent by the microprocessor 130, and inflate the cuff 133 according to the inflating signal.

In embodiments of the present disclosure, when the device for monitoring fatigue driving is adopted for monitoring, the cuff 133 may be wound around the driver's head. Thus, when the driving module 131 inflates the cuff 133, along with the gradually increased pressure intensity of the gas in the cuff 133, the cuff 133 may impose pressure on the driver's head, which is helpful for increasing the amount of blood supply on the driver's head. Therefore, it is helpful for the driver to restore from the fatigue driving state to the clearheaded driving state.

Figure 3:
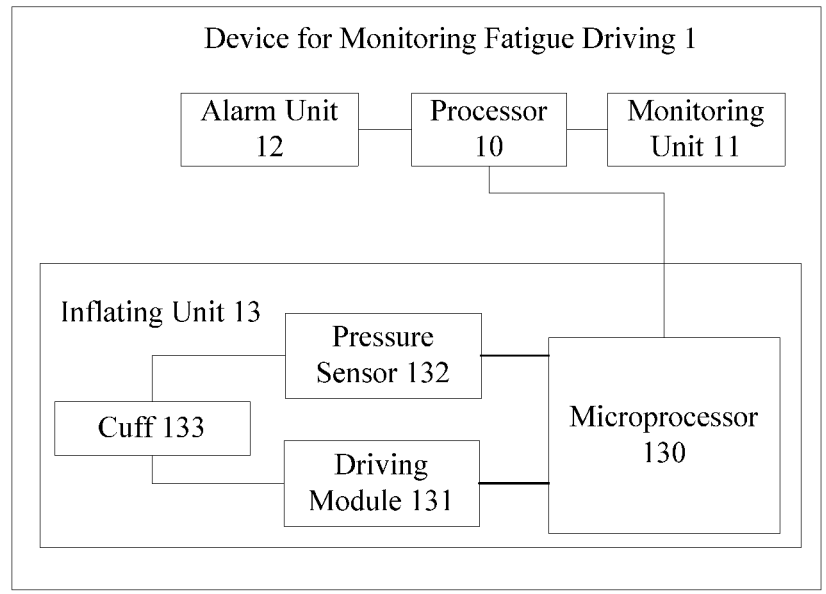
FIG. 3 is a third schematic structural view of a device for monitoring fatigue driving provided by an embodiment of the present disclosure.

For instance, as shown in FIG. 3, the inflating unit 13 may also include a pressure sensor 132 connected with both the microprocessor 130 and the cuff 133.

For instance, the pressure sensor 132 may be configured to detect a value of a pressure intensity of the cuff 133 when the driving module 131 inflates the cuff 133, and send the value of the pressure intensity to the microprocessor 130.

The microprocessor 130 is also configured to receive the value of the pressure intensity sent by the pressure sensor 132, and send a deflating signal to the driving module 131 when the pressure intensity is greater than or equal to a default threshold.

The driving module 131 is also configured to receive the deflating signal sent by the microprocessor 130, and deflate the cuff 133 according to the deflating signal.

In embodiments of the present disclosure, the driving module 131 in the inflating unit 13 may inflate the cuff 133, so that the pressure intensity in the cuff 133 can be gradually increased. That is, the cuff 133 can apply pressure to the driver's brain, which is helpful for increasing the amount of blood supply on the driver's head, and hence it is helpful for the driver to restore from the fatigue driving state to the clearheaded driving state.

Moreover, when the driving module 131 inflates the cuff 133, in order to prevent the cuff 133 from applying too much pressure to the driver's head and prevent the driver's head from being overly oppressed, the pressure sensor 132 may detect a value of the pressure intensity of the cuff 133 in real time and send the value of the pressure intensity to the microprocessor 130. The microprocessor 130 can compare the value of the pressure intensity with a default threshold (that is, a predetermined maximal pressure intensity applied to the cuff). If the microprocessor 130 determines that the value of the pressure intensity is greater than or equal to the default threshold, the microprocessor 130 may send the deflating signal to the driving module 131 and control the driving module 131 to deflate the cuff 133, so as to reduce the pressure applied to the driver's head by the cuff 133, and hence the brain of the driver may not be overly oppressed.

For instance, the default threshold may be set according to actual design demands of the inflating unit. No specific limitation will be given here in embodiments of the present disclosure.

For instance, in embodiments of the present disclosure, after the driving module 131 inflates the cuff 133 which is helpful for the driver to restore from the fatigue driving state to the clearheaded driving state, the microprocessor 130 may also send the deflating signal to the driving module 131 after a preset time and instruct the driving module 131 to deflate the cuff 133, so as to avoid the problem that the driver's head is overly oppressed due to overlarge pressure caused by the cuff 133 on the brain of the driver when the driver is in the clearheaded driving state.

An implementation principle of the inflating unit 13 in embodiments of the present disclosure is similar to an implementation principle of inflating in a process of measuring blood pressure via an electronic sphygmomanometer; that is, a cuff being worn around an arm of a user to be tested is inflated, so that the cuff can impose certain pressure to the user's arm. For instance, the implementation principle of the inflating unit 13 may be understood with reference to the implementation principle of inflating in the process of measuring blood pressure via an electronic sphygmomanometer. No further description will be given here.

For instance, in a feasible implementation, the driving module 131 in embodiments of the present disclosure may be a miniature inflation motor. As the miniature inflation motor not only can inflate the cuff 133 but also can deflate the cuff 133, the driving module 131 may be implemented by one miniature inflation motor.

For instance, in another feasible implementation, the driving module 131 in embodiments of the present disclosure may include a miniature pressure pump and a miniature exhaust valve. As the miniature pressure pump inflates the cuff 133 and the miniature exhaust valve deflates the cuff 133, the driving module 131 may be implemented by one miniature pressure pump and one miniature exhaust valve together.

It is noted that the miniature inflation motor, the miniature pressure pump and the miniature exhaust valve in embodiments of the present disclosure may all be selected as components with a small size, so as to prevent the inflating unit and the device for monitoring fatigue driving from interfering with normal driving of the driver.

For instance, the monitoring unit 11 may include at least one of a face monitoring module 110 or a brain monitoring module 111.

For instance, the face monitoring module 110 may be configured to monitor the eyes of the driver, and send data indicating a state of the eyes of the driver to the processor 10.

The brain monitoring module 111 may be configured to monitor the brain of the driver, and send data indicating a brain state of the driver to the processor 10.

It is noted that: when the monitoring unit 11 includes the face monitoring module 110, the data indicating the driving state of the driver sent by the monitoring unit 11 to the processor 10 includes data indicating a facial state of the driver (for instance, the data indicating the facial state may include data indicating the eye state). When the monitoring unit 11 includes the brain monitoring module 111, the data indicating the driving state of the driver sent by the monitoring unit 11 to the processor 10 may include data indicating the brain state of the driver. When the monitoring unit 11 includes the face monitoring module 110 and the brain monitoring module 111, the data indicating the driving state of the driver sent by the monitoring unit 11 to the processor 10 includes data indicating the facial state of the driver, data indicating the eye state of the driver, data indicating the brain state of the driver or any combination thereof.

Correspondingly, the monitoring result includes a face monitoring result corresponding to the face monitoring module 110 and a brain monitoring result corresponding to the brain monitoring module 111. The face monitoring result is used for indicating that the face and/or the eyes of the driver are in the fatigue state, and the brain monitoring result is used for indicating that the brain of the driver is in the fatigue state.

For instance, when the monitoring unit 11 includes the face monitoring module 110, the monitoring result which can be acquired by the processor 10 includes the face monitoring result; when the monitoring unit 11 includes the brain monitoring module 111, the monitoring result which can be acquired by the processor 10 includes the brain monitoring result; and when the monitoring unit 11 includes the face monitoring module 110 and the brain monitoring module 111, the monitoring result which can be acquired by the processor 10 includes the face monitoring result and the brain monitoring result.

Figure 4:
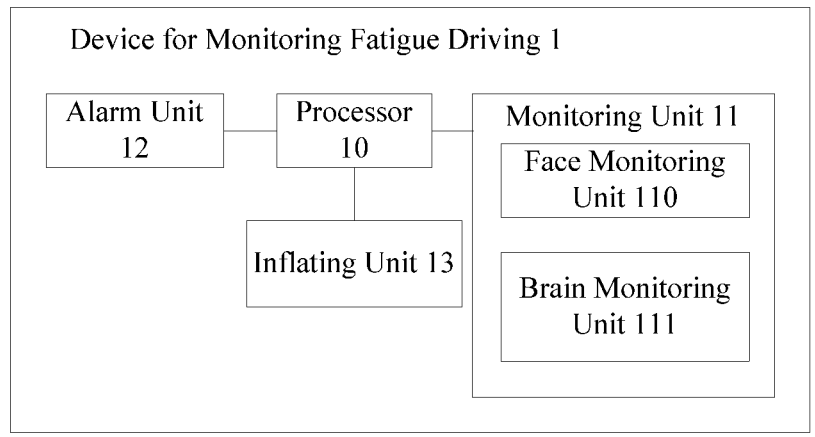
FIG. 4 is a fourth schematic structural view of a device for monitoring fatigue driving provided by an embodiment of the present disclosure.

For instance, with reference to FIG. 1, the monitoring unit 11 as shown in FIG. 4 in embodiments of the present disclosure may be implemented by the face monitoring module 110 and the brain monitoring module 111 together. For instance, the eye state of the driver may be monitored by the face monitoring module 110 and simultaneously the brain state of the driver may be monitored by the brain monitoring module 111, so that whether the driver is in the fatigue driving state may be determined according to the driver's state monitored by the two monitoring modules including the face monitoring module 110 and the brain monitoring module 111. Hence, the monitoring accuracy of the device for monitoring fatigue driving can be improved.

For instance, the face monitoring module 110 may be a miniature camera, and the brain monitoring module 111 may be an EEG sensor. For instance, the miniature camera may monitor the eye state of the driver in real time by extracting eye features of the driver. The miniature camera may also monitor the facial state of the driver in real time by extracting facial features of the driver. The EEG sensor may monitor the brain state of the driver in real time by acquiring EEG signals of the driver.

In some embodiments, the face monitoring module 110 may be implemented by a miniature camera and may also be achieved by other component/apparatus/devices capable of capturing the eye features of the driver. No specific limitation will be given in the present disclosure. An EEG sensor may also be selected according to actual design demands of the device for monitoring fatigue driving. No specific limitation will be given in the present disclosure.

It is noted that the miniature camera, the EEG sensor and the like may be selected as components with small sizes, so as to prevent the monitoring unit and the device for monitoring fatigue driving from interfering with normal driving of the driver.

In embodiments of the present disclosure, the miniature camera for implementing the face monitoring module 110 may capture the eye features of the driver by using camera-capture technologies, so that whether the eyes of the driver are in the fatigue state can be determined according to the eye features. For instance, the miniature camera may take pictures capturing eyes of the driver. The pictures may reflect physiological changes of the driver, that is, the changes of the eye features of the driver, e.g., an amplitude of wink, a frequency of wink, and an average eye closing time of the driver, etc. The miniature camera or the processor may determine whether the eyes of the driver are in the fatigue state by analyzing the eye features of the driver in the pictures.

Of course, the miniature camera for implementing the face monitoring module 110 in embodiments of the present disclosure may also monitor the facial features, eye signals, head movement characteristics and the like of the driver, and can also determine whether the driver is in the fatigue driving state by synthesizing all the information. The specific monitoring method is similar to the method of monitoring the eye features of the driver via the miniature camera. No further description will be given here.

It is noted that the implementation principle of the EEG sensor is similar to a general electrocardiogram (ECG) monitoring principle, and both utilize electrodes to monitor voltage variations. For instance, a neuronal activity of the brain is transmitted to a cerebral cortex through ions to form weak electric signals; after sensing the weak electric signals, the electrodes in the EEG sensor may perform differential amplification, filtering, digital-to-analog conversion and the like on the weak electric signals, so as to convert the weak electric signals into initial data of EEG Thus, the EEG sensor or the processor can determine whether the brain of the driver is in the fatigue state by analyzing the initial data of EEG.

For instance, in embodiments of the present disclosure, the EEG sensor for implementing the brain monitoring module 111 or the processor may determine whether the brain of the driver is in the fatigue state by adoption of an EEG fatigue state determination method using independent component analysis (ICA). For instance, the EEG sensor may acquire EEG signals (that is, the initial data of EEG) by the above method, and the EEG sensor or the processor may perform ICA analysis on the acquired EEG signals, calculate a variety of power spectral densities in the EEG, and calculate a fatigue index according to the variety of power spectral densities. When the calculated fatigue index is greater than 1, the brain of the driver may be determined to be in the fatigue state. For instance, the fatigue index may be calculated by the following method.

Illustratively, an EEG signal of a human being may be decomposed into 4 basic rhythms, e.g., a δ wave, a θ wave, an α wave and a β wave, and the 4 rhythms will change along with the change of the fatigue state of the human being. For instance, when the α wave and β wave dominate, it indicates that the consciousness of the human being is clearheaded; but when the δ wave and θ wave dominate, it indicates that the consciousness of the human being is blurred and even is in a slight sleep state. Therefore, whether the brain of the human being is in the fatigue state may be determined and estimated by calculation and analysis of the EEG signals of the human being.

The frequency ranges corresponding to the δ wave, θ wave, α wave and β wave are respectively −3.8 Hz, 4-7.8 Hz, 8-12.8 Hz and 13-30 Hz. Supposing the power spectral density is P and the fatigue index is F, if:

$E_\delta = \Sigma P_i, 1 \leq f(i) \leq 3.8$; $E_\theta = \Sigma P_i, 4 \leq f(i) \leq 7.8$; $E_\alpha = \Sigma P_i, 8 \leq f(i) \leq 12.8$; $E_\beta = \Sigma P_i, 13 \leq f(i) \leq 30$, in which $$i = 1, 2, 3, \ldots, \frac{N}{2}, \text{ and } f = (i) = \frac{f_s i}{N},$$

then $$F = \frac{E_\delta + E_\theta}{E_\alpha + E_\beta}.$$

Figure 5:
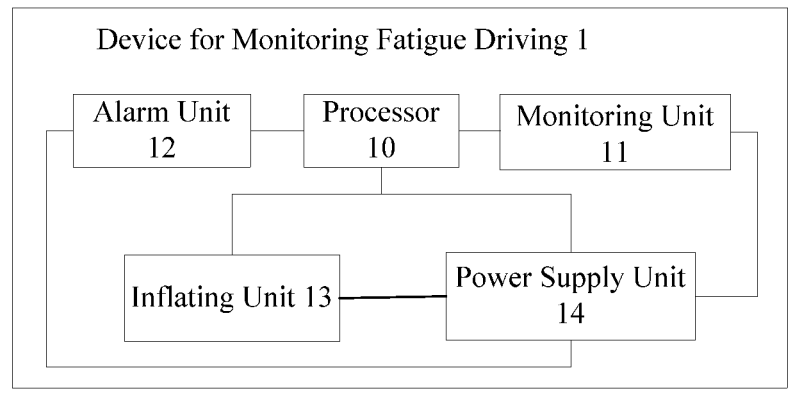
FIG. 5 is a sixth schematic structural view of a device for monitoring fatigue driving provided by an embodiment of the present disclosure.

For instance, as shown in FIG. 5, the device 1 for monitoring fatigue driving provided by embodiments of the present disclosure may further comprise a power supply unit 14 connected with the processor 10, the monitoring unit 11, the alarm unit 12 and the inflating unit 13 respectively.

In some embodiments, the power supply unit 14 is configured to supply power for the processor 10, the monitoring unit 11, the alarm unit 12 and the inflating unit 13.

In embodiments of the present disclosure, as the power supply unit 14 is adopted to supply power for the processor 10, the monitoring unit 11, the alarm unit 12 and the inflating unit 13, it is ensured that the processor 10, the monitoring unit 11, the alarm unit 12 and the inflating unit 13 can all operate normally, so that the device for monitoring fatigue driving provided by embodiments of the present disclosure can accurately monitor the driving state of the driver and perform corresponding operations that match the driving state.

For instance, the power supply unit 14 may be charged by a wireless charging approach, e.g., being charged by a power source mounted on a vehicle. As the power supply unit 14 in embodiments of the present disclosure is charged by a wireless charging approach, interference on the driving of the driver when the power supply unit is charged by a wired approach can be avoided.

Figure 6:
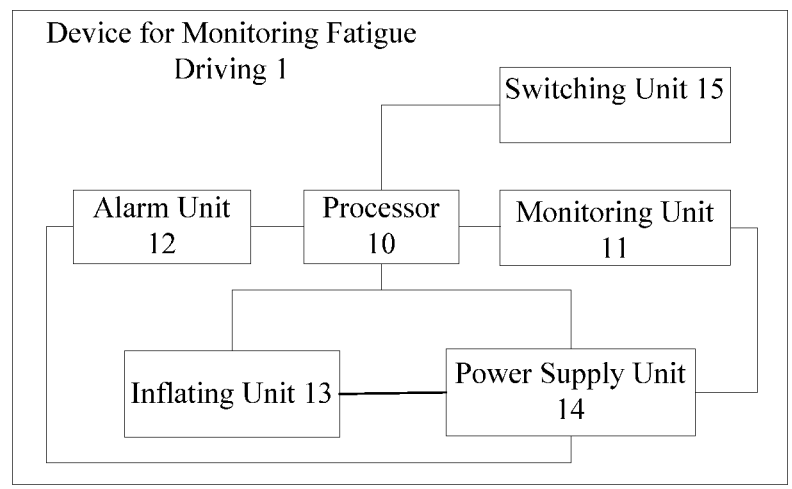
FIG. 6 is a sixth schematic structural view of a device for monitoring fatigue driving provided by an embodiment of the present disclosure.

For instance, as shown in FIG. 6, the device 1 for monitoring fatigue driving provided by embodiments of the present disclosure may further comprise a switching unit 15 connected with the processor 10. The switching unit 15 may be configured to control the device 1 for monitoring fatigue driving to switch on or off.

It should be understood that: in order to reduce the power consumption of the device for monitoring fatigue driving, the switching unit 15 may be adopted to control the device for monitoring fatigue driving to switch on when the device is used; and the switching unit 15 may be adopted to control the device for monitoring fatigue driving to switch off when the device is not used, so that controllability of the device for monitoring fatigue driving can be achieved.

For instance, the switching unit 15 may be a mechanical switch or an acceleration sensor.

When the switching unit 15 is a mechanical switch, the driver may control the device for monitoring fatigue driving to switch on or off by operating on the mechanical switch. When the switching unit 15 is an acceleration sensor, if the driver is driving a vehicle, the acceleration sensor may determine that the driver is in the driving state by detecting the acceleration of the vehicle, and automatically trigger and switch on the device for monitoring fatigue driving. In the above two ways, the mechanical switch can be easily implemented and also has a lower cost; but the acceleration sensor has better real-time performance and reliability.

For instance, the alarm unit 12 may include at least one of a voice alarm module or a vibrating motor alarm module. For instance, the voice alarm module may be implemented by a loudspeaker; that is, the voice alarm module may provide a voice alarm signal through the loudspeaker. The vibrating motor alarm module may be implemented by a motor; that is, the vibrating motor alarm module may provide a vibrating alarm signal through motor rotation.

Figure 7:
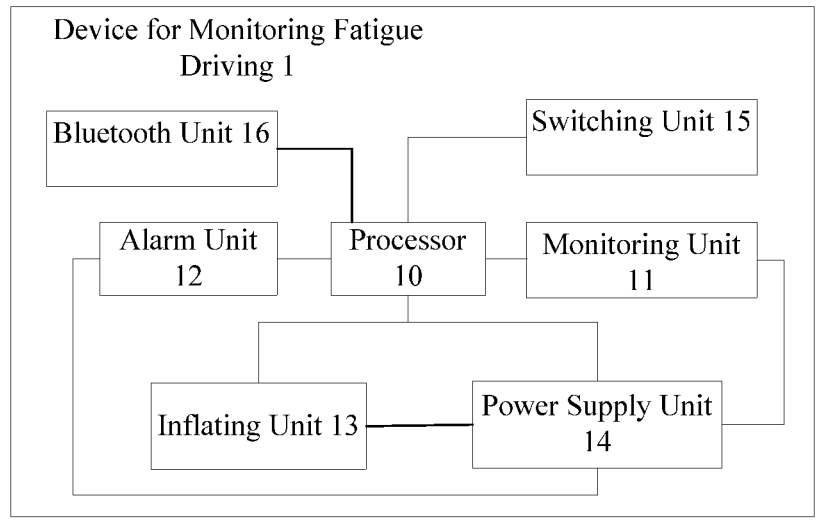
FIG. 7 is a seventh schematic structural view of a device for monitoring fatigue driving provided by an embodiment of the present disclosure.

For instance, as shown in FIG. 7, the device 1 for monitoring fatigue driving provided by embodiments of the present disclosure may further comprise a Bluetooth unit 16 connected with the processor 10. For instance, the Bluetooth unit 16 may be interactive with other devices. The Bluetooth unit 16 may also include a Bluetooth headset, so that the driver can answer a call during driving. In embodiments of the present disclosure, the Bluetooth unit 16 may be powered by batteries and/or may also be powered by the power supply unit 16. No specific limitation will be given in the present disclosure.

Embodiments of the present disclosure provide a device for monitoring fatigue driving. The device for monitoring fatigue driving comprises a processor and a monitoring unit, an alarm unit and an inflating unit which are respectively connected with the processor. The processor is configured to acquire a monitoring result, send an alarm instruction to the alarm unit according to the monitoring result, and send an inflating instruction to the inflating unit if acquiring the monitoring result again after sending the alarm instruction. The monitoring result is used for indicating that the driver is in the fatigue driving state; the alarm instruction is used for instructing the alarm unit to give out an alarm; and the inflating instruction is used for instructing the inflating unit to perform an inflation operation. The monitoring unit is configured to monitor the driving state of the driver in real time, and send data indicating the driving state of the driver to the processor. The alarm unit is configured to receive the alarm instruction sent by the processor, and give out an alarm according to the alarm instruction. The inflating unit is configured to receive the inflating instruction sent by the processor, and perform an inflation operation according to the inflating instruction.

Based on the above technical solutions, the device for monitoring fatigue driving provided by the present disclosure may monitor the driving state of the driver in real time in the monitoring process, and give out an alarm when the driver is in the fatigue driving state, so as to prompt the driver that he/she is in the fatigue driving state. The device for monitoring fatigue driving may perform an inflation operation if it is detected that the driver continues to be in the fatigue driving state after giving out the alarm. As the inflating operation can result in an extrusion pressing with a certain intensity on the driver's body, it is helpful for the driver to restore from the fatigue driving state to the clearheaded driving state, so that the probability that the driver restores from the fatigue driving state to the clearheaded driving state can be increased, and hence the probability of safety problems emerging when the driver is in the fatigue driving state can be reduced.

Figure 8:
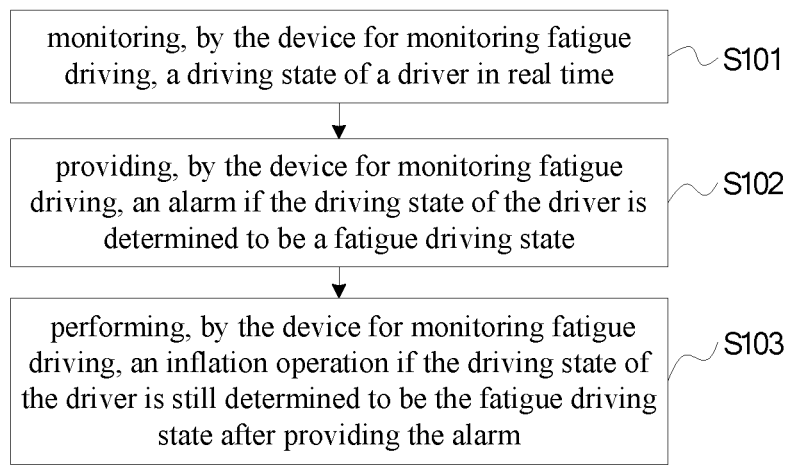
FIG. 8 is a first flowchart of a method for monitoring fatigue driving provided by an embodiment of the present disclosure.

For instance, as shown in FIG. 8, embodiments of the present disclosure provide a method for monitoring fatigue driving. The method may be applied to the device for monitoring fatigue driving as shown in any one of FIGS. 1-7. The detailed description on the device for monitoring fatigue driving may be with reference to with the relevant description as shown in FIGS. 1-7. No further description will be given here. The method may comprise:

S101: monitoring, by the device for monitoring fatigue driving, a driving state of a driver in real time.

S102: providing, by the device for monitoring fatigue driving, an alarm if the driving state of the driver is determined to be a fatigue driving state. For instance, the device for monitoring fatigue driving may give out a voice, light or vibrating alarm signal.

S103: performing, by the device for monitoring fatigue driving, an inflation operation if the driving state of the driver is still determined to be the fatigue driving state after providing the alarm. The inflating operation helps the driver to restore to a clearheaded driving state.

In embodiments of the present disclosure, the device for monitoring fatigue driving may monitor the driving state of the driver in real time, give out an alarm to prompt the driver that he/she is in the fatigue driving state when the driving state of the driver is the fatigue driving state, and perform an inflation operation if it is continuously detected that the driver is still in the fatigue driving state after giving out the alarm. As the inflating operation can result in extrusion pressing with certain intensity on the driver's body, it is helpful for the driver to restore from the fatigue driving state to the clearheaded driving state, so that the probability that the driver restores from the fatigue driving state to the clearheaded driving state can be improved, and hence the probability of safety problems emerging when the driver is in the fatigue driving state can be reduced.

For instance, a specific form and structure of the device for monitoring fatigue driving and an implementation principle of the inflating operation of the device for monitoring fatigue driving may all be provided with reference to relevant description in the above embodiment. No further description will be given here.

Figure 9:
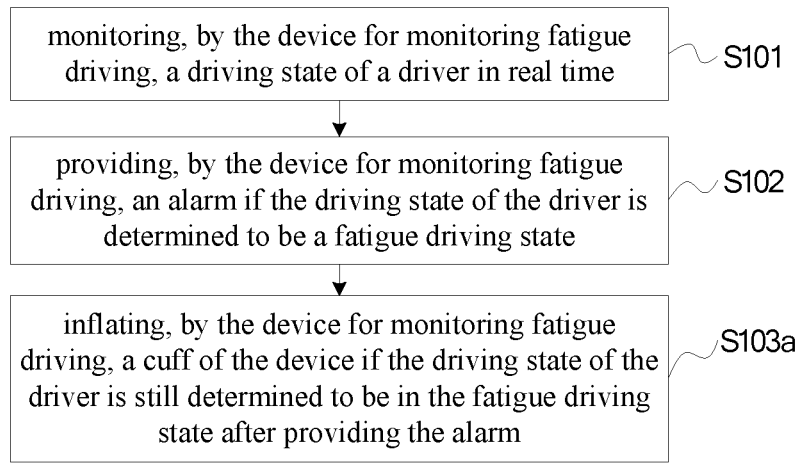
FIG. 9 is a second flowchart of a method for monitoring fatigue driving provided by an embodiment of the present disclosure.

For instance, as shown in FIG. 9, in the method for monitoring fatigue driving provided by embodiments of the present disclosure, the step S103 may include:

S103a: inflating, by the device for monitoring fatigue driving, a cuff of the device if the driving state of the driver is still determined to be in the fatigue driving state after providing the alarm. The detailed description on the cuff may be provided with reference to relevant description on the cuff in the above embodiments. No further description will be given here.

Figure 10:
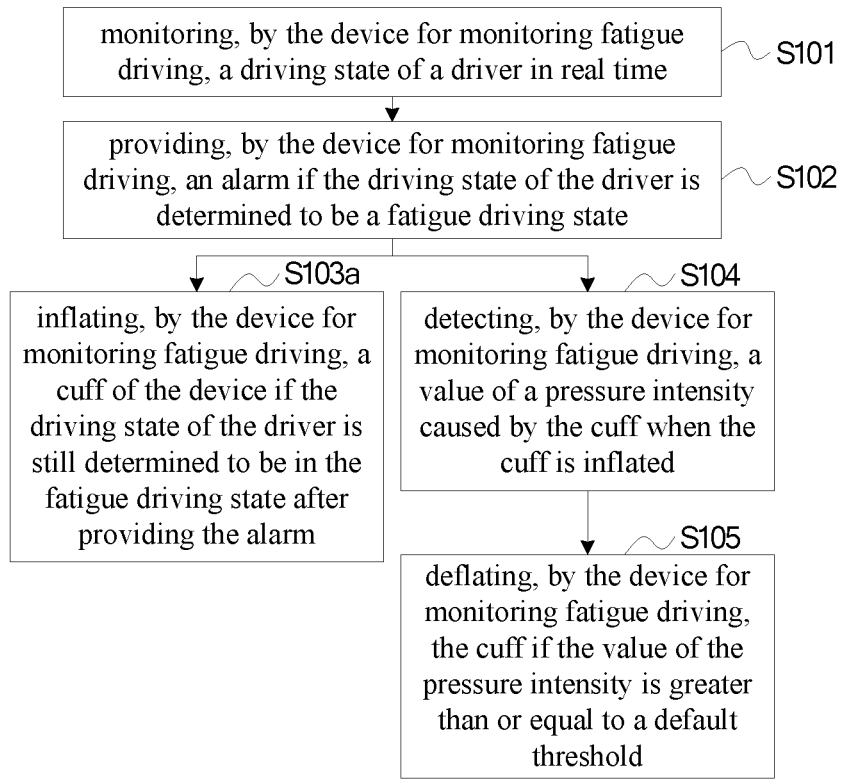
FIG. 10 is a third flowchart of a method for monitoring fatigue driving provided by an embodiment of the present disclosure.

For instance, as shown in FIG. 10, the method for monitoring fatigue driving provided by embodiments of the present disclosure may further comprise:

S104: detecting, by the device for monitoring fatigue driving, a value of a pressure intensity caused by the cuff when the cuff is inflated.

S105: deflating, by the device for monitoring fatigue driving, the cuff if the value of the pressure intensity is greater than or equal to a default threshold.

Moreover, in the process of inflating the cuff by the device for monitoring fatigue driving, in order to prevent the brain of the driver from being overly oppressed by an overlarge pressure of the cuff on the brain of the driver, the device for monitoring fatigue driving may detect a value of the pressure intensity of the cuff in real time, and deflate the cuff when the value of the pressure intensity is greater than or equal to the default threshold, so that the pressure of the cuff applied on the brain of the driver can be reduced, and hence the brain of the driver cannot be overly oppressed.

The default threshold may be set according to actual design demands of the device for monitoring fatigue driving. No specific limitation will be given in the present disclosure.

In embodiments of the present disclosure, the implementation principle of the deflating operation by the device for monitoring fatigue driving may be provided with reference to relevant description in the above embodiments. No further description will be given here.

It should be noted that: in embodiments of the present disclosure, the steps S104-S105 may be simultaneously executed when the step S103 is executed, so as to avoid the problem that the brain of the driver is overly oppressed due to overlarge pressure of the cuff on the brain of the driver when the device for monitoring fatigue driving continuously inflates the cuff.

Figure 11:
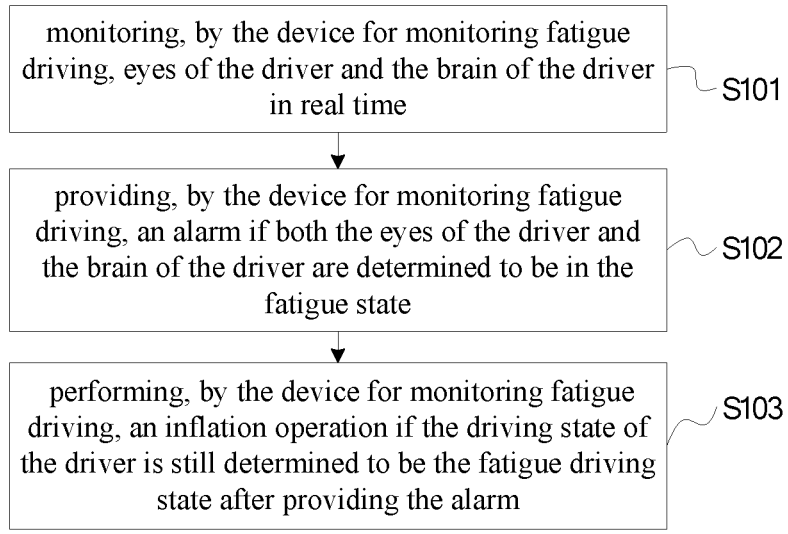
FIG. 11 is a fourth flowchart of a method for monitoring fatigue driving provided by an embodiment of the present disclosure.

For instance, with reference to FIG. 8, as shown in FIG. 11, in the method for monitoring fatigue driving provided by embodiments of the present disclosure, the steps S101 and S102 may include:

S101a: monitoring, by the device for monitoring fatigue driving, eyes of the driver and the brain of the driver in real time.

S102a: providing, by the device for monitoring fatigue driving, an alarm if both the eyes of the driver and the brain of the driver are determined to be in the fatigue state.

The method for monitoring fatigue driving provided by embodiments of the present disclosure simultaneously monitors whether the eyes of the driver are in the fatigue state and whether the brain of the driver is in the fatigue state, can determine whether the driver is in the fatigue driving state according to the two monitoring results, and hence can improve the monitoring accuracy of the device for monitoring fatigue driving.

Figure 12:
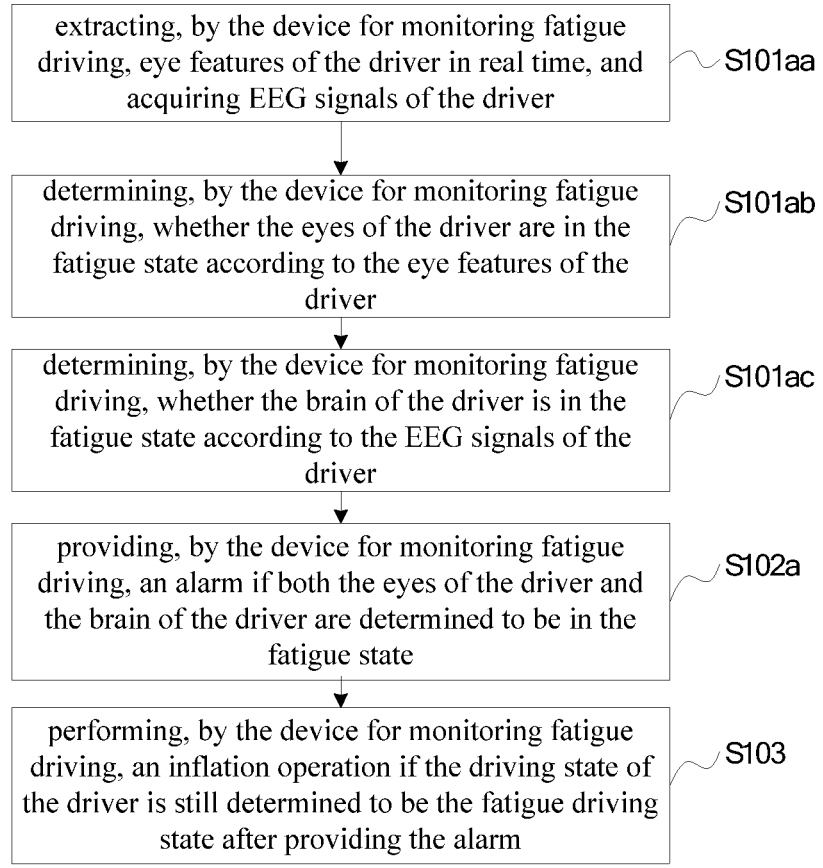
FIG. 12 is a fifth flowchart of a method for monitoring fatigue driving provided by an embodiment of the present disclosure.

For instance, as shown in FIG. 12, in the method for monitoring fatigue driving provided by embodiments of the present disclosure, the step S101a may include:

S101aa: extracting, by the device for monitoring fatigue driving, eye features of the driver in real time, and acquiring EEG signals of the driver.

S101ab: determining, by the device for monitoring fatigue driving, whether the eyes of the driver are in the fatigue state according to the eye features of the driver.

S101ac: determining, by the device for monitoring fatigue driving, whether the brain of the driver is in the fatigue state according to the EEG signals of the driver.

For instance, the method of determining whether the driver is in the fatigue driving state by monitoring the eye features of the driver and the EEG signals of the driver, which is performed by the device for monitoring fatigue driving, and specific hardware to implement the method may be provided with reference to relevant description in the above embodiments. No further description will be given here.

Embodiments of the present disclosure provide a method for monitoring fatigue driving, in which the device for monitoring fatigue driving is adopted to monitor the driving state of the driver in real time. If the driving state of the driver is the fatigue driving state, the device for monitoring fatigue driving gives out an alarm; and if the driving state of the driver is still in the fatigue driving state after giving out the alarm, the device for monitoring fatigue driving performs an inflation operation.

Based on the above technical solutions, the device for monitoring fatigue driving provided by the present disclosure may monitor the driving state of the driver in real time in the monitoring process, and give out an alarm when the driver is in the fatigue driving state, so as to prompt the driver that he/she is in the fatigue driving state, and perform an inflation operation if it is continuously detected that the driver is still in the fatigue driving state after giving out the alarm. As the inflating operation can result in extrusion pressing with certain intensity on the driver's body, it is helpful for the driver to restore from the fatigue driving state to the clearheaded driving state, so that the probability that the driver restores from the fatigue driving state to the clearheaded driving state can be improved, and hence the probability of occurrence of safety problems when the driver is in the fatigue driving state can be reduced.

The processor or microprocessor included in the device for monitoring fatigue driving in embodiments of the disclosure may include various computing architectures such as a complex instruction set computer (CISC) architecture, a reduced instruction set computer (RISC) architecture or an architecture for implementing a combination of multiple instruction sets. The memory may store instructions and/or data executed by the processor. The instructions and/or data may include codes which are configured to achieve some functions or all the functions of one or more devices in the embodiments of the present disclosure. For instance, the memory includes a dynamic random access memory (DRAM), a static random access memory (SRAM), a flash memory, an optical memory or other memories well known to those skilled in the art.

It should be clearly understood by those skilled in the art that the foregoing is only illustrative for convenient and simple description, and other similar embodiments may also be provided in actual application.

It should be understood that the functional modules disclosed in several embodiments of the application may be implemented by other means. For instance, the structural modules described above are only illustrative. Moreover, the displayed or discussed connection may be connection via some pins, and may be electrical connection.

The units described as discrete components may be or may not be physically separate, and components displayed as units may be or may not be physical units, may be disposed at one place or may also be distributed on a plurality of units. Partial or all the units may be selected according to actual demands to achieve the objectives of the proposals of the embodiments.

In addition, the functional units in the embodiments of the present disclosure may be integrated into a processing unit, or various units may be independently physically provided, or two or more than two units may be integrated into one unit. The integrated units may be implemented by hardware and may also be implemented by software functional units In the present disclosure, terms such as "first", "second" and the like used in the present disclosure do not indicate any sequence, quantity or significance but only for distinguishing different constituent parts. Also, the terms such as "a," "an," or "the" etc., are not intended to limit the amount, but indicate the existence of at lease one. The terms "comprises," "comprising," "includes," "including," etc., are intended to specify that the elements or the objects stated before these terms encompass the elements or the objects and equivalents thereof listed after these terms, but do not preclude the other elements or objects.

What are described above is related to the illustrative embodiments of the disclosure only and not limitative to the scope of the disclosure; any changes or replacements easily for those technical personnel who are familiar with this technology in the field to envisage in the scopes of the disclosure, should be in the scope of protection of the present disclosure. Therefore, the scopes of the disclosure are defined by the accompanying claims.

The present application claims the priority of the Chinese Patent Application No. 201510170673.6 filed on Apr. 10, 2015, which is incorporated herein by reference in its entirety as part of the disclosure of the present application.

What is claimed is:

1. A device for monitoring fatigue driving, comprising a processor, and a monitoring unit, an alarm unit and an inflating unit which are respectively connected with the processor, wherein:

the processor is configured to acquire a monitoring result, send an alarm instruction to the alarm unit according to the monitoring result, and send an inflating instruction to the inflating unit when acquiring the monitoring result again after sending the alarm instruction, wherein the monitoring result is used for indicating whether a driver is in a fatigue driving state, the alarm instruction is used for instructing the alarm unit to give out an alarm, and the inflating instruction is used for instructing the inflating unit to perform an inflation operation;

the monitoring unit is configured to monitor the driving state of the driver in real time, and send data indicating the driving state of the driver to the processor;

the alarm unit is configured to receive the alarm instruction sent by the processor, and give out the alarm according to the alarm instruction; and the inflating unit is configured to receive the inflating instruction sent by the processor, and perform the inflation operation according to the inflating instruction, wherein the inflating unit includes a microprocessor connected with the processor, a driving module connected with the microprocessor, and a cuff connected with the driving module, wherein:

the microprocessor is configured to receive the inflating instruction sent by the processor, and send an inflating signal to the driving module according to the inflating instruction;

the driving module is configured to receive the inflating signal sent by the microprocessor, and inflate the cuff according to the inflating signal;

wherein the cuff is wound around the driver's head to impose pressure on the driver's head when it is inflated so as to increase the amount of blood supply on the driver's head.

2. The device for monitoring fatigue driving according to claim 1, wherein the inflating unit further includes a pressure sensor connected with both the microprocessor and the cuff, wherein:

the pressure sensor is configured to detect a value of a pressure intensity of the cuff when the driving module inflates the cuff, and send the value of the pressure intensity to the microprocessor;

the microprocessor is also configured to receive the value of the pressure intensity sent by the pressure sensor, and send a deflating signal to the driving module when the value of the pressure intensity is greater than or equal to a default threshold; and the driving module is also configured to receive the deflating signal sent by the microprocessor, and deflate the cuff according to the deflating signal.

3. The device for monitoring fatigue driving according to claim 2, wherein:

the driving module is a miniature inflation motor; or the driving module includes a miniature pressure pump and a miniature exhaust valve.

4. The device for monitoring fatigue driving according to claim 1, wherein:

the driving module is a miniature inflation motor; or the driving module includes a miniature pressure pump and a miniature exhaust valve.

5. The device for monitoring fatigue driving according to claim 1, wherein the monitoring unit includes at least one of a face monitoring module or a brain monitoring module;

the face monitoring module is configured to monitor eyes of the driver and send data indicating an eye state of the driver to the processor; and the brain monitoring module is configured to monitor a brain of the driver and send data indicating a brain state of the driver to the processor.

6. The device for monitoring fatigue driving according to claim 5, wherein:

the face monitoring module is a miniature camera; and the brain monitoring module is an electroencephalogram (EEG) sensor.

7. The device for monitoring fatigue driving according to claim 1, wherein the device for monitoring fatigue driving further comprises a power supply unit connected with the processor, the monitoring unit, the alarm unit and the inflating unit; and the power supply unit is configured to supply power for the processor, the monitoring unit, the alarm unit and the inflating unit.

8. The device for monitoring fatigue driving according to claim 7, wherein:

the power supply unit is charged by a wireless charging approach.

9. The device for monitoring fatigue driving according to claim 1, wherein the device for monitoring fatigue driving further comprises a switching unit connected with the processor; and the switching unit is configured to control the device for monitoring fatigue driving to switch on or off.

10. The device for monitoring fatigue driving according to claim 9, wherein:

the switching unit is a mechanical switch or an acceleration sensor.

11. The device for monitoring fatigue driving according to claim 1, wherein:

the alarm unit includes at least one of a voice alarm module or a vibrating motor alarm module.

12. The device for monitoring fatigue driving according to claim 1, further comprising a switching unit connected with the processor, wherein the switching unit is configured to control the device for monitoring fatigue driving to switch on or off.

13. A method for monitoring fatigue driving, applied in a device for monitoring fatigue driving according to claim 1, comprising:

monitoring, by the device for monitoring fatigue driving, a driving state of a driver in real time;

providing, by the device for monitoring fatigue driving, an alarm if the driving state of the driver is determined to be a fatigue driving state; and performing, by the device for monitoring fatigue driving, an inflation operation if the driving state of the driver is still determined to be the fatigue driving state after providing the alarm.

14. The method according to claim 13, wherein performing, by the device for monitoring fatigue driving, the inflation operation if the driving state of the driver is still determined to be the fatigue driving state after providing the alarm includes:

inflating a cuff of the device for monitoring fatigue driving if the driving state of the driver is still determined to be the fatigue driving state after providing the alarm.

15. The method according to claim 14, further comprising:

detecting, by the device for monitoring fatigue driving, a value of a pressure intensity of the cuff when the cuff is inflated; and deflating the cuff if the value of the pressure intensity is greater than or equal to a default threshold.

16. The method according to claim 13, wherein:

monitoring, by the device for monitoring fatigue driving, the driving state of a driver in real time includes:

monitoring, by the device for monitoring fatigue driving, eyes of the driver and a brain of the driver in real time; and performing, by the device for monitoring fatigue driving, the inflation operation if the driving state of the driver is still determined to be the fatigue driving state after providing the alarm includes:

providing, by the device for monitoring fatigue driving, the alarm if both the eyes of the driver and the brain of the driver are determined to be in a fatigue state.

17. The method according to claim 16, wherein monitoring, by the device for monitoring fatigue driving, the eyes of the driver and the brain of the driver in real time includes:
- extracting, by the device for monitoring fatigue driving, eye features of the driver in real time, and acquiring an EEG signal of the driver;
- determining, by the device for monitoring fatigue driving, whether the eyes of the driver are in the fatigue state according to the eye features; and
- determining, by the device for monitoring fatigue driving, whether the brain of the driver is in the fatigue state according to the EEG signal.

* * * * *